(12) United States Patent
Jang

(10) Patent No.: US 11,627,957 B2
(45) Date of Patent: Apr. 18, 2023

(54) SUTURE AND METHOD FOR PRODUCING SAME

(71) Applicant: JWORLD CO., LTD., Chungcheongbuk-do (KR)

(72) Inventor: Min-Seo Jang, Seoul (KR)

(73) Assignee: JWORLD CO., LTD., Chungcheongbuk-Do (KR)

( * ) Notice: Subject to any disclaimer, the term of this patent is extended or adjusted under 35 U.S.C. 154(b) by 223 days.

(21) Appl. No.: 17/146,671

(22) Filed: Jan. 12, 2021

(65) Prior Publication Data

US 2021/0128148 A1 May 6, 2021

Related U.S. Application Data

(62) Division of application No. 15/773,679, filed as application No. PCT/KR2016/012712 on Nov. 7, 2016, now Pat. No. 10,918,378.

(30) Foreign Application Priority Data

Nov. 5, 2015 (KR) .......................... 10-2015-0155148

(51) Int. Cl.
*A61B 17/06* (2006.01)
*D02G 3/44* (2006.01)
*D02J 3/02* (2006.01)
*A61B 17/00* (2006.01)

(52) U.S. Cl.
CPC ......... *A61B 17/06166* (2013.01); *D02G 3/44* (2013.01); *D02J 3/02* (2013.01); *A61B 2017/00004* (2013.01); *A61B 2017/00526* (2013.01); *A61B 2017/00792* (2013.01); *A61B 2017/06176* (2013.01)

(58) Field of Classification Search
CPC .... A61B 2017/0435; A61B 2017/0429; A61B 2017/0427; A61B 2017/0412; A61B 2017/00579; A61B 5/6839; A61B 17/1796; A61B 17/06052; A61B 2017/0414; A61B 2017/00349; A61B 5/6883; A61B 2017/06176; A61B 2017/06171; A61B 17/06166; D02G 3/448

See application file for complete search history.

(56) References Cited

U.S. PATENT DOCUMENTS

2009/0312791 A1* 12/2009 Lindh, Sr. ........ A61B 17/06166
606/228

* cited by examiner

*Primary Examiner* — Stella K Yi
(74) *Attorney, Agent, or Firm* — The PL Law Group, PLLC

(57) ABSTRACT

A suture according to an embodiment of the present disclosure includes a first barb portion, a second barb portion, and a center portion which connects the first barb portion and the second barb portion to each other. Each of end portions of the first barb portion and the second barb portion may be formed so as to face the center portion, and a hole portion including a plurality of holes may be formed in at least one of the first barb portion, the second barb portion, and the center portion. The suture may show an excellent recovery and a lifting effect to be semi-permanently maintained and may have an excellent strength.

9 Claims, 5 Drawing Sheets

SUTURE AND METHOD FOR PRODUCING SAME

CROSS REFERENCE TO RELATED APPLICATIONS AND CLAIM OF PRIORITY

This application is a divisional application of U.S. application Ser. No. 15/773,679, filed on May 4, 2018, which is a National Stage entry from International Application No. PCT/KR2016/012712, filed Nov. 7, 2016, which claims priority to the benefit of Korean Patent Application No. 10-2015-0155148 filed in the Korean Intellectual Property Office on Nov. 5, 2015, the entire contents of which are incorporated herein by reference.

BACKGROUND

1. Field

The present invention relates to a suture and a method for producing same.

2. Description of the Related Art

Suturing is important in a surgical operation for various reasons. Suturing is performed on a patient whose face skin or oral mucous membrane is torn or for a cosmetic purpose and is considered as one of complete operations. In addition, performing of delicate and cosmetically excellent suturing is an important factor in determining success or failure of an operation.

As a material of a suture (stitching fiber), natural materials and synthetic materials may be used. The suture has absorption or non-absorption characteristics depending on the material. As natural materials for the absorbable suture, catgut, chromic, gut, and the like may be used, and as synthetic materials for the absorbable suture, polyglycolic acid (Dexon and Maxon), polyglactin (Vicryl), polydioxanone (PDS), and the like may be used. As natural materials for the non-absorbable suture, silk may be used. As synthetic materials for the non-absorbable suture, polyester (Dacron), polypropylene (Prolene), polyamide (Nylon), e-PTFE (Gore-tex), and the like may be used.

The suture has long been used for joining or suturing of damaged muscle, blood vessel, nerve tissue, wound, and surgical incision. Also, the suture is used in double eyelid surgery or non-invasive surgery for removing wrinkle, and laxity of skin or tissue generated due to aging, reduction in skin elasticity, external wound, overuse, necrosis, and the like.

Recently, a suture having barbs formed on a surface thereof has been developed and used. These sutures have an excellent anchoring ability due to the barb, thus there is an advantage in that the sutured incision is not easily released after suturing.

Non-invasive face lifting using the suture is a technique of pulling and removing wrinkle by lifting sagging skin and tissue of face, chin, neck, abdomen, vagina, chest, hip, and the like by a needle and thread without using a knife. Since it is possible to minimize a scar and decrease bleeding and swelling without excessive skin incision, the face lifting is getting into the spotlight.

SUMMARY

An object of the present invention is to provide a suture excellent in suturing without a knot.

Another object of the present invention is to provide a suture excellent for recovery of a sutured area.

Another object of the present invention is to provide a suture excellent in effects of non-invasive face lifting.

Another object of the present invention is to provide a suture capable of providing semi-permanent lasting non-invasive face lifting effects.

Another object of the present invention is to provide various types of sutures suitable for being used in various methods and sites of non-invasive surgery.

The above objects of the present invention will be achieved by the following features:

(1) A method for manufacturing a suture, including: a first step of heating a suture raw material under a predetermined temperature condition; a second step of pressurizing the suture raw material heated in the first step and performing compression-molding; and a third step of forming cutting lines in a first edge and a second edge of a compression-molded suture product formed in the second step and forming a barb portion by applying a tensile force to the compression-molded suture product having the cutting lines formed therein, wherein the cutting lines are continuously formed with being spaced apart from each other at a predetermined interval in a state of being inclined at a constant angle toward one direction or both directions of the first edge and the second edge.

(2) The method for manufacturing a suture of according to the above (1), further including: a step of forming a hole portion, wherein a plurality of holes are continuously formed with being spaced apart from each other in the compression-molded suture product.

(3) The method for manufacturing a suture of according to the above (1), wherein, when forming the cutting lines in the third step, the cutting lines are formed for forming a plurality of holes which are continuously formed with being spaced apart from each other in the compression-molded suture product.

(4) The method for manufacturing a suture of according to the above (1), wherein the suture includes a first barb portion, a second barb portion, and a center portion which connects the first barb portion and the second barb portion to each other, each of end portions of the first barb portion and the second barb portion is formed so as to face the center portion, and a hole portion including a plurality of holes is formed in at least one of the first barb portion, the second barb portion, and the center portion.

(5) The method for manufacturing a suture of according to the above (1), wherein, in the third step, the barb portion is divided into a first barb portion and a second barb portion, and the barb portion is formed to connect the first barb portion and the second barb portion to each other by the center portion.

(6) The method for manufacturing a suture of according to the above (1), wherein the preset temperature is a melting point of the suture raw material or lower or a glass transition temperature of the suture raw material or higher.

(7) The method for manufacturing a suture of according to the above (1), wherein the pressurization is performed two to four times in the compression-molding step.

(8) The method for manufacturing a suture of according to the above (1), wherein the step of forming the barb portion further includes a step of applying a rotational force to the suture having the cutting lines formed therein.

(9) A suture including: a first barb portion; a second barb portion; and a center portion which connects the first barb portion and the second barb portion to each other, wherein each of end portions of the first barb portion and the second barb portion is formed so as to face the center portion, and a hole portion including a plurality of holes is formed in at least one of the first barb portion, the second barb portion, and the center portion.

(10) The suture of claim (9), further including: a first distal portion and a second distal portion at each of distal portions of the first barb portion and the second barb portion, which is not connected to the center portion.

(11) The suture of claim (10), wherein at least one of the first distal portion and the second distal portion has a hole portion including a plurality of holes formed therein.

(12) The suture of claim (9) or (11), the hole has a diameter of 50 μm to 300 μm.

(13) The suture of claim (9), the hole portion is positioned in at least the center portion.

(14) The suture of claim (9), the hole portions are positioned in at least the first barb portion and the second barb portion.

(15) The suture of claim (9), the hole portions are positioned in at least the center portion, the first barb portion, and the second barb portion.

(16) The suture of claim (11), the hole portions are positioned in the first barb portion, the second barb portion, the first distal portion, and the second distal portion.

(17) The suture of claim (11), the hole portions are positioned in the first barb portion, the second barb portion, the center portion, and the first distal portion, and the second distal portion.

(18) A suture, including: a first barb portion; a second barb portion; a center portion which connects the first barb portion and the second barb portion to each other; and a first distal portion and a second distal portion at each of distal portions of the first barb portion and the second barb portion, which is not connected to the center portion, wherein at least one of the first distal portion and the second distal portion has a hole portion including a plurality of holes formed therein.

(19) The suture of claim (18), the hole has a diameter of 50 μm to 300 μm.

The suture according to the present invention is excellent for suturing without a knot.

The suture according to the present invention is excellent for recovery of a sutured area after suturing.

The suture according to the present invention is excellent in effects of non-invasive face lifting.

The suture according to the present invention is capable of providing semi-permanent lasting non-invasive face lifting effects.

Since the suture according to the present invention uses a yarn of which an orientation is determined, crystallinity thereof is low, flexibility is good, and tensile strength and elongation are excellent compared to using a preform having orientation characteristics obtained by an injection molding method, etc.

Strength of the suture according to the present invention is not greatly reduced compared to a normal suture which does not include a barb and a hole.

Various types of sutures according to the present invention may be effectively used in various different methods and sites of non-invasive surgery.

DETAILED DESCRIPTION

Figure 1:
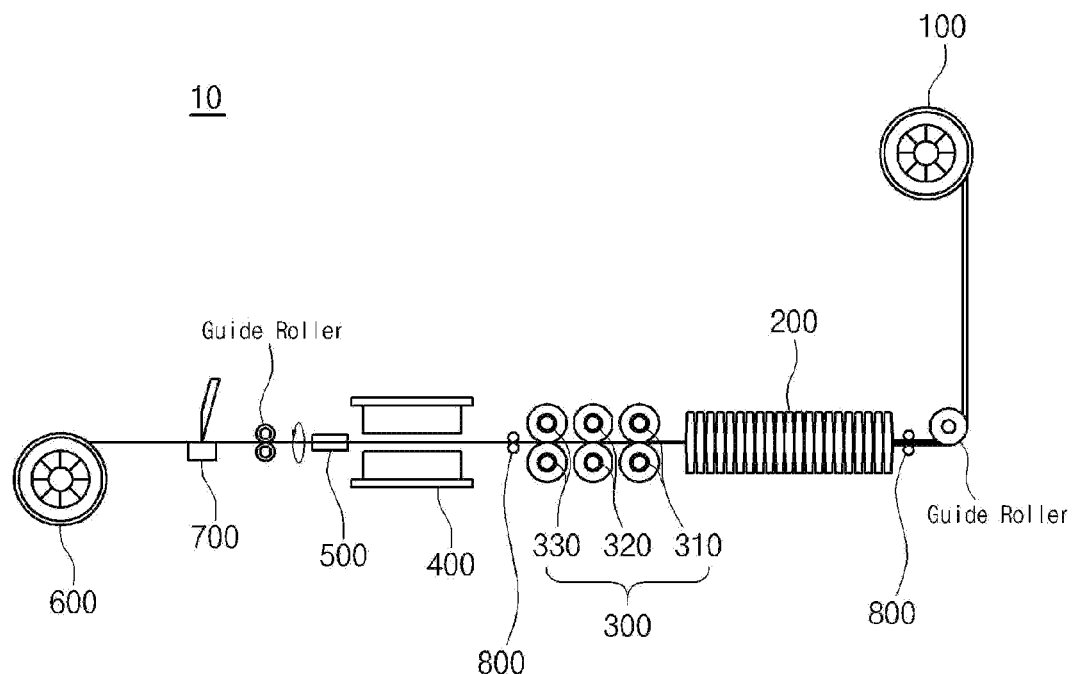
FIG. 1 is a view illustrating a suture manufacturing apparatus including a preheating unit as an embodiment of a suture manufacturing apparatus to which a method of manufacturing a suture of the present invention is implemented.

The present invention discloses a suture and a method for manufacturing the same. The method for manufacturing a suture includes: a first step of heating a suture raw material under a predetermined temperature condition, a second step of pressurizing the suture raw material heated in the first step and performing a compression-molding, and a third step of forming cutting lines in a first edge and a second edge of a compression-molded suture product formed in the second step and forming a barb portion by applying a tensile force to the compression-molded suture product having the cutting lines formed therein, wherein the cutting lines are continuously formed with being spaced apart from each other at a predetermined interval in a state of being inclined at a constant angle toward one direction or both directions of the first edge and the second edge. Therefore, it is possible to manufacture the suture which is excellent for recovery of a sutured area and is capable of semi-permanent lasting non-invasive face lifting effects while providing an excellent strength.

When using a suture having barbs formed on a surface thereof in non-invasive face lifting, there is an advantage of effectively supporting tissue by the barbs of the suture. Meanwhile, when using an absorbable suture, a supporting force by the suture disappears due to a fact that the absorbable suture is degraded and absorbed, the non-invasive face lifting should be performed again after a constant period.

In order to solve above problem, the present invention provides a suture having barbs formed on a surface thereof and a hole portion including a plurality of holes further formed therein, and a method for manufacturing the same. The suture manufactured by using the method of the present invention induces surrounding tissue cells of the inserted suture to get in the hole of the suture and to form a new tissue, therefore it is effective for semi-permanent lasting wrinkle removal effects obtained by the face lifting. In addition, although the suture manufactured by using the method of the present invention includes the barbs and holes, there is an advantage of not greatly reducing the suture strength.

Hereinafter, a method for manufacturing a suture of the present invention will be described in detail. In the present disclosure, singular forms are intended to include plural forms unless the context clearly indicates otherwise.

Hereinafter, for the purpose of explaining, the method for manufacturing a suture will be described with reference to FIGS. 1 and 2 which illustrate two embodiments of the suture manufacturing apparatus to which the method for manufacturing a suture of the present invention is applied.

As medical suture raw materials of the present invention, absorbable and non-absorbable biomedical polymers may be used. More specifically, an absorbable biomedical polymer including at least one selected from the group consisting of polydioxanone, poly-(1-lactic) acid, polyglycolic acid, polycaprolactone, and a copolymer thereof, and an absorbable biomedical polymer including at least one selected from the group consisting of polypropylene, nylon and a mixture thereof may be used.

Before performing compression-molding the suture raw material, a step of heating a suture raw material is performed. Crystallinity of a polymer is deteriorated by exerting heat on the polymer, thereby providing excellent environment for workability, but it may affect to an orientation of the suture. Thus, it is preferable that the heating is performed under conditions that do not affect properties of the raw material suture. At this time, the heating temperature is equal to or greater than a glass transition temperature (Tg) of a raw material, and equal to or less than a melting point (Tm) of the raw material, and preferably in a range of a melting point of the raw material—15° C. (Tm—15° C.) to a melting point of the raw material—30° C. (Tm—30° C.). According to an embodiment, the suture raw material is supplied through a suture supply unit 100 and may be heated by a preheating unit 200. According to another embodiment, the suture raw material may be heated with a pressing roller including a heating wire described below without a separate preheating unit.

As described above, the suture manufacture by using the method including the step of heating the suture raw material before performing compression-molding uses a yarn of which an orientation is determined, crystallinity thereof is low, flexibility is good, and tensile strength and elongation are excellent compared with using a preform having orientation characteristics obtained by using an injection molding method and the like.

According to an embodiment, the preheating unit 200 may be manufactured in a cylindrical shape, and in this case, the heating wire is installed inside a wall of the preheating unit. Therefore, it may be configured in such a way that a temperature of a preheater can be controlled by a temperature control unit based on the required temperature.

In the step of pressurizing the heated suture raw material and performing compression-molding, the heated suture raw material is pressurized using the pressing roller to obtain a compression-molded suture product.

When pressurizing the suture raw material and performing compression, the suture becomes flatten and of which a portion which contacts a pair of pressing rollers forms a flat surface, and of which a portion which does not contact the pressing roller forms a convex and narrow edge. In this case, one of two flat surfaces is referred to as an upper surface of the suture and the other thereof is referred to as a lower surface of the suture, and one of two convex and narrow edges is referred to as a first edge of the suture and the other thereof is referred to as a second edge of the suture. In addition, the shortest distance between the upper surface and the lower surface is referred to as a thickness of the suture and the shortest distance between the first edge and the second edge is referred to as a width of the suture.

According to an embodiment, in a case of a final compression-molded suture product after completing the pressurization and compression-molding, it is possible to obtain a final compression-molded suture product having a thickness of 10% to 60% with respect to a diameter of an initial suture raw material and having a width of 1.5 times to 6 times with respect to the diameter of the initial suture raw material. For example, a final compression-molded suture product having a thickness of 50% with respect to a diameter of an initial suture raw material and having a width of 3 times with respect to the diameter of the initial suture raw material may be obtained.

According to an embodiment, the suture may have a width of 300 μm or more and 2000 μm or less, but it is not limited thereto. The suture may have a width narrower or wider than the above-described range, as necessary.

The compression-molding step may be performed through two to four times of pressurization and compression.

When pressurizing the suture raw material and performing compression-molding, if molding the suture by performing only one time of pressurization, the orientation thereof is lost to cause a reduction in a strength. Thus, it is preferable that the suture raw material is compressed and molded two to four times so as to allow the suture raw material to be processed gradually thin for securing the orientation.

According to an embodiment, the suture raw material may be gradually compressed by repeating two to four times of pressurizations using a pair of pressing rollers. According to another embodiment, the suture raw material may be gradually compressed using two to four pairs of pressing rollers. The respective pressing rollers may be installed in parallel so as to be rotated independently from each other.

According to an embodiment, it is possible to include an adjuster that can adjust an interval between the pressing rollers so as to control a thickness of the compression-molded suture product to a micrometer unit.

Figure 2:
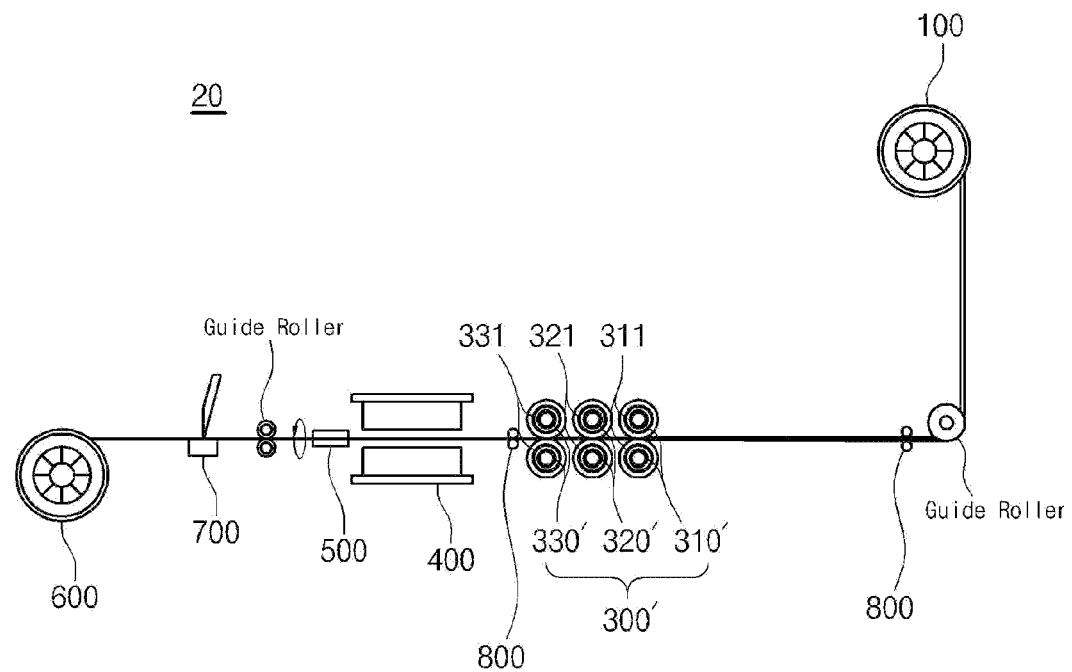
FIG. 2 is a view illustrating a suture manufacturing apparatus without a preheating unit as an embodiment of the suture manufacturing apparatus to which the method for manufacturing a suture of the present invention is implemented.

FIGS. 1 and 2 illustrate an embodiment of a suture manufacturing apparatus provided with a pressing roller unit 300 including three pairs of pressing rollers.

In a case of using three pairs of pressing rollers, a pair of first pressing rollers 310, a pair of second pressing rollers 320, and a pair of third pressing rollers 330 which are disposed in this order are used. It is configured that the second pressing rollers 320 pressurize the suture raw material more than the first pressing rollers 310 and the third pressing rollers 330 pressurize the suture raw material more than the second pressing rollers 320, so as to allow the suture raw material to be processed in a gradually flattened form.

In this case, an interval between an upper end and a lower end of a frame formed in the first pressing rollers 310 may be set so as to pressurize the suture raw material in a level of 50% to 80% of an initial diameter thereof, and the second pressing rollers 320 may pressurize again the first compression-molded suture product from the first pressing rollers 310. At this time, an interval between an upper end and a lower end of a frame formed in the second pressing rollers 320 may be set so as to pressurize the first compression-molded suture product from the first pressing rollers 310 in a level of 50% to 80% of the thickness thereof. Finally, an interval between an upper end and a lower end of a frame formed in the third pressing rollers 330 may also be set to pressurize the second compression-molded suture product from the second pressing rollers 320 in a level of 50% to 80% of the thickness thereof.

According to an embodiment, in order to heat the suture raw material at an appropriate temperature when pressurizing the suture raw material and performing compression-molding, all the pressing rollers 310, 320 and 330 may include the heating wire. As described above, in a case of including the heating wire, the preheating unit 200 may not be used.

After completing the pressurization and compression-molding, one or both of a step of forming a barb portion and a step of forming a hole portion are performed.

In the step of forming the barb portion, cutting lines are formed in the first edge and the second edge of the final compression-molded suture product, which are continuously formed with being spaced apart from each other at a predetermined interval, and barb-shaped projections are formed by applying only a tensile force only or both the tensile force and a rotational force to the compression-molded suture product having the cutting lines formed therein. In the present disclosure, the term 'barb' means such a barb-shaped projection.

According to an embodiment, the step of forming the barb portion may be performed by a die-cutting mold unit 400. The die-cutting mold unit 400 is used for forming the cutting lines on both sides of the suture in a length direction by pressurizing the final compression-molded suture product and is configured to form the cutting lines for forming the barbs at the first edge and the second edge of the suture compressed in a flattened form by passing through the pressing roller unit 300. According to a more specific embodiment, the above-described cutting lines may be formed by a knife, a laser beam, injection molding by pressing, stamping and the like, but it is not limited thereto.

The injection molding by pressing is configured to form the cutting lines on the compression-molded suture product after press processing. In this case, an upper mold or a lower mold may have a cutting member such as a blade so as to continuously form the cutting lines in a state of being inclined at a constant angle with respect to the first edge and the second edge of the suture. In this case, the cutting lines which are formed on both sides may be formed in one direction or two directions.

After forming the cutting lines on the compression-molded suture product, only the tensile force or both the tensile force and the rotational force are applied to the compression-molded suture product, thus to form the suture having the barb portion formed therein. At this time, the barb portion may be formed in one direction or two directions.

According to an embodiment, applying the tensile force to the compression-molded suture product may be performed by a tensioner 800. The tensioner 800 may be disposed at a previous stage of the preheating unit 200 and at a subsequent stage of the pressing roller unit 300.

According to an embodiment, applying the rotational force to the compression-molded suture product may be performed by a twisting unit 500. The twisting unit 500 is used for continuously applying the rotational force to the compression-molded suture product to twist the same and is configured to fix one side of the suture in which the cutting lines are formed while rotating the other side thereof, thus to twist the entire raw material in a spiral form. Therefore, a suture is formed in a shape in which the raw material of a band form is twisted, that is, the raw material is twisted in a state of having the barbs formed therein. According to this, 90° of rotation per 1 cm of the suture is applied thereto, to form the barbs in a spiral form. When inserting the suture into a soft tissue, the suture has an anchoring ability in a direction opposite to the inserted direction thereof.

In the step of forming the hole portion, holes are formed in the compression-molded suture product.

Any one or both of the step of forming the hole portion and the step of forming the barb portion may be performed, as necessary. When performing both of the steps of forming the hole portion and the barb portion, these steps of forming the hole portion and the barb portion may be performed at the same time, or the step of forming the hole portion may be performed before or after the step of forming the barb portion.

Figure 3:
FIG. 3 is a view illustrating a suture manufactured according to an embodiment of the present invention.

FIG. 3 illustrates a suture manufactured according to an embodiment of the present invention in which the hole portion is not formed, and only the tensile force is applied without applying the rotational force. According to the embodiment of FIG. 3, the first barb portion and the second barb portion are positioned on both sides of a center portion which is located in the center of the suture, such that the first barb portion and the second barb portion are connected to each other about the center portion, and each of ends of the barbs is formed so as to face the center portion.

The hole portion may be formed so as to include one or a plurality of holes along a central axis of the compression-molded suture product parallel with a length direction thereof.

FIGS. 4 to 13 illustrate sutures having hole portions formed therein, respectively, according to embodiments of the present invention.

FIGS. 4 to 7 illustrate sutures which include a first barb portion, a second barb portion, and a center portion that connects the first barb portion, and in which each of end portions of the barb portions is formed so as to face the center portion while having hole portions formed therein, respectively, according to embodiments of the present invention.

Figure 4:
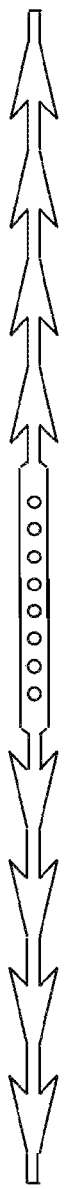
FIG. 4 is a view illustrating a suture manufactured according to an embodiment of the present invention.

FIG. 4 illustrates a suture in which the hole portion is formed in only the center portion thereof according to an embodiment of the present invention.

Figure 5:
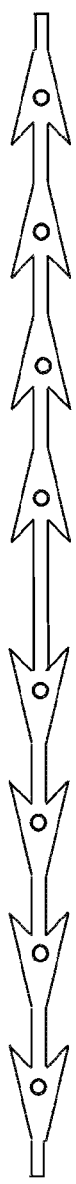
FIG. 5 is a view illustrating a suture manufactured according to an embodiment of the present invention.
Figure 6:
FIG. 6 is a view illustrating a suture manufactured according to an embodiment of the present invention.

FIGS. 5 and 6 illustrate sutures in which the hole portions are formed in only the barb portions thereof, respectively, according to an embodiment of the present invention.

Figure 7:
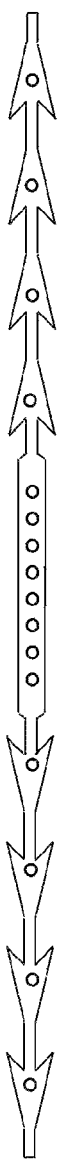
FIG. 7 is a view illustrating a suture manufactured according to an embodiment of the present invention.

FIG. 7 illustrates a suture in which the hole portions are formed in the center portion and the barb portions thereof according to an embodiment of the present invention.

FIGS. 8 to 13 illustrate sutures including a first barb portion, a second barb portion, a center portion which connects the first barb portion and the second barb portion to each other, and a first distal portion which is connected to an end of the first barb portion on a side opposite to the center portion and a second distal which is connected to an end of the second barb portion on a side opposite to the center portion, and each of ends of the barbs is formed so as to face the center portion while having hole portions formed therein, respectively, according to embodiments of the present invention.

Figure 8:
FIG. 8 is a view illustrating a suture manufactured according to an embodiment of the present invention.
Figure 9:
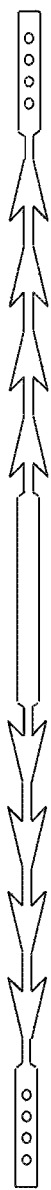
FIG. 9 is a view illustrating a suture manufactured according to an embodiment of the present invention.

FIGS. 8 and 9 illustrate sutures in which the hole portions are formed in only distal portions thereof, respectively, according to an embodiment of the present invention.

Figure 10:
FIG. 10 is a view illustrating a suture manufactured according to an embodiment of the present invention.
Figure 11:
FIG. 11 is a view illustrating a suture manufactured according to an embodiment of the present invention.

FIGS. 10 and 11 illustrate sutures in which the hole portions are formed in the distal portions and the barb portions thereof, respectively, according to an embodiment of the present invention.

Figure 12:
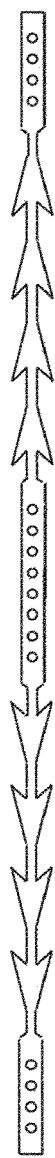
FIG. 12 is a view illustrating a suture manufactured according to an embodiment of the present invention.

FIG. 12 illustrates a suture in which the hole portions are formed in the distal portions and the center portion thereof according to an embodiment of the present invention.

Figure 13:
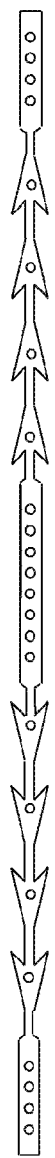
FIG. 13 is a view illustrating a suture manufactured according to an embodiment of the present invention.

FIG. 13 illustrates a suture in which the hole portions are formed in the center portion and the barb portions thereof according to an embodiment of the present invention.

The suture manufactured according to the present invention may be used suitably for various methods and sites of non-invasive surgery different from each other depending on the positions of the hole portions. Examples of non-invasive surgery which may particularly use the suture having the hole portions at various positions are as follows. But, these are merely described as an example, it does not mean that each type of the sutures is only useful in non-invasive surgery described below.

According to an embodiment, the suture having the hole portion in the center portion is useful for non-invasive face lifting which is performed by folding a suture in half. In this case, since the hole portion is positioned at a folded portion in a U shape, when performing non-invasive face lifting, the hole portion of the suture is positioned above a jawline (for example, near eyebrow or ear), an end thereof on a side opposite to the folded portion is positioned on the jawline side.

According to another embodiment, the suture having the hole portions in both distal portions is useful for non-invasive face lifting which is performed by folding a suture in half. In this case, since the hole portion of the suture is not positioned at a folded portion in a U shape but is positioned at an end thereof on a side opposite to the folded portion, when performing non-invasive face lifting, the hole portion of the suture is positioned at the jawline, and the end thereof on the side opposite to the folded portion (for example, near eyebrow or ear) is positioned above the jawline.

Further, according to another embodiment, the suture having the hole portion in the barb portion is useful for non-invasive surgery which uses a suture itself without folding a short suture.

The hole of the hole portion may have a diameter of 50 μm to 1000 μm. For example, the hole may have a diameter of 50 μm to 500 μm, 50 μm to 300 μm, 100 μm to 500 μm, 200 μm to 800 μm, and the like, and preferably, 50 μm to 300 μm.

When a distance between a hole and an edge of the suture is too close or a distance between one hole and an adjacent hole is too close, the strength of the suture may be greatly reduced. Therefore, it is preferable that the interval between the hole and the edge of the suture and the interval between the hole and the edge of the suture are set in an appropriate range. According to an embodiment, the interval between the hole and the edge of the suture may be 50 μm to 1000 μm. For example, the interval may be 50 μm to 500 μm, 50 μm to 300 μm, 100 μm to 500 μm, 200 μm to 800 μm, and the like, and preferably, 50 μm to 300 μm. The interval between one hole and the adjacent hole may be 300 μm or more, and preferably, 500 μm or more.

According to an embodiment, the hole may be formed by a knife, a laser beam, injection molding by pressing, stamping, and the like, but it is not limited thereto. According to an embodiment, an apparatus for forming the hole portion may be positioned in the die-cutting mold unit 400. In this case, forming the cutting lines for forming the barb portion and forming the cutting lines for forming the hole portion may be performed at the same time. According to another embodiment, an apparatus for forming the hole portion may be positioned at the front or rear of a separate die-cutting mold unit 400 other than the die-cutting mold unit 400, the hole portion may be formed in a previous stage or a subsequent stage of the forming the cutting lines for forming the barb portion.

The prepared suture having one or both of the barb portion and the hole portion formed therein may be wound in a roll by a suture winding unit 600. A cutting unit 700 may be disposed between the die-cutting mold unit 400 and the suture winding unit 600, thus cut the suture so as to be wound in a constant length.

What is claimed is:

1. A suture comprising:
   a first barb portion; a second barb portion; and a center portion which connects the first barb portion and the second barb portion to each other,
   wherein each of end portions of the first barb portion and the second barb portion is formed so as to face the center portion; and
   a hole portion including a plurality of holes is formed in at least one of the first barb portion, the second barb portion, and the center portion,
   wherein the hole has a diameter of 50 μm to 300 μm.

2. The suture of claim 1, further comprising:
   a first distal portion and a second distal portion at each of distal portions of the first barb portion and the second barb portion which are not connected to the center portion.

3. The suture of claim 2, wherein at least one of the first distal portion and the second distal portion has a hole portion including a plurality of holes formed therein.

4. The suture of claim 1, wherein the hole portion is positioned in at least the center portion.

5. The suture of claim 1, wherein the hole portions are positioned in at least the first barb portion and the second barb portion.

6. The suture of claim 1, wherein the hole portions are positioned in at least the center portion, the first barb portion, and the second barb portion.

7. The suture of claim 3, wherein the hole portions are positioned in the first barb portion, the second barb portion, the first distal portion, and the second distal portion.

8. The suture of claim 3, wherein the hole portions are positioned in the first barb portion, the second barb portion, the center portion, and the first distal portion, and the second distal portion.

9. A suture, comprising:
   a first barb portion;
   a second barb portion; a center portion which connects the first barb portion and the second barb portion to each other; and
   a first distal portion and a second distal portion at each of distal portions of the first barb portion and the second barb portion which are not connected to the center portion,
   wherein at least one of the first distal portion and the second distal portion has a hole portion including a plurality of holes formed therein,
   wherein the hole has a diameter of 50 μm to 300 μm.

* * * * *